United States Patent [19]

Leopold et al.

[11] 4,080,446

[45] Mar. 21, 1978

[54] SUPPRESSION OF THROMBOCYTE AGGREGATION

[75] Inventors: Götz Leopold; Reinhard Lissner; Jürgen Maisenbacher; Werner Mehrhof; Joachim Gante, all of Darmstadt, Germany

[73] Assignee: Merck Patent Gesellschaft mit beschrankter Haftung, Darmstadt, Germany

[21] Appl. No.: 738,952

[22] Filed: Nov. 4, 1976

[30] Foreign Application Priority Data

Nov. 7, 1975 Germany .............................. 2549998

[51] Int. Cl.$^2$ .................... A61K 31/42; A61K 31/625
[52] U.S. Cl. ..................................... 424/232; 424/272
[58] Field of Search ............................... 424/272, 232

[56] References Cited

U.S. PATENT DOCUMENTS 3,933,840  1/1976  Dahm et al. ......................... 424/272

OTHER PUBLICATIONS

Merck Index, 7th Ed. 1960, p. 13.
Chem. Abst. vol. 83–1975, p. 188378v.

Primary Examiner—Stanley J. Friedman
Attorney, Agent, or Firm—Millen and White

[57] ABSTRACT 2-(4,5-bis-p-chlorophenyloxazol-2-yl-mercapto)-propionic acid and its physiologically acceptable salts is useful for suppressing aggregation of thrombocytes, particularly when administered in combination with aspirin.

13 Claims, No Drawings

SUPPRESSION OF THROMBOCYTE AGGREGATION

BACKGROUND OF THE INVENTION

This invention relates to a method and compositions for the inhibition of the aggregation of thrombocytes in mammals.

It is known to administer compounds which inhibit the aggregation of thombocytes to prevent or reduce the likelihood of the occurrence of thrombo-embolism in various primary diseases. Acetylsalicyclic acid (ASA) is used for this purpose, especially in micro-encapsulated form. However, there are disadvantages in using this compound. For example, a very high dose can be required (in the case of thrombophlebitis, for example, 3 g. per day are recommended), and high doses of ASA frequently not well tolerated. Furthermore, this compound has a significant influence on haemostasis only as a result of an action on the thrombocyte function.

2-(4,5-bis-p-chlorophenyl-oxazol-2-yl-mercapto)-propionic acid (I) and it physiologically acceptable salts, are known to have useful antiphlogistic activities. See U.S. Pat. No. 3,933,840.

It is an object of this invention to provide a novel method and compositions for the inhibition of thrombocyte aggregation in mammals, especially humans, e.g., for prophylaxis and therapy in cases involving risk of arterial or venous thrombosis. Other objects will be apparent to those skilled in the art.

SUMMARY OF THE INVENTION

In a composition aspect, this invention relates to pharmaceutical compositions comprising a thrombocyte aggregation inhibiting mixture of 2-(4,5-bis-p-chlorophenyl-oxazol-2-yl-mercapto)-propionic acid, or a physiologically acceptable salt thereof, and acetylsalicylic acid or a physiologically acceptable salt thereof.

In a process aspect, this invention relates to a method of inhibiting thrombocyte aggregation in human patients in which there exists a high risk of arterial or venous thrombosis, which comprises administering thereto an amount of 2-(4,5-bis-p-chlorophenyl-oxazol-2-yl-mercapto)-propionic acid or a physiologically acceptable salt thereof, alone or in admixture with acetylsalicylic acid or a physiologically acceptable salt thereof, effective to inhibit thrombocyte aggregation.

DETAILED DISCUSSION

Compound I and its salts are able to suppress, even after administration thereof is terminated, the aggregation of thrombocytes induced by SP 54 (sodium pentosanpolysulfate). Investigations were carried out with the aid of the platelet aggregation test according to K. Breddin (Thrombos. Diathes. heamorrh. Supplement 27 (1968)). This aggregation inhibitory effect is sustained for many days after administration of I is discontinued, which is consistent with the slow elimination of I from the body. The re-emergence of the thrombocyte aggregation which can be induced with SP 54 can be ascribed to the slowly falling serum level of I. The influence on the thrombocyte function in the sense of an inhibition of aggregation (adhesion) can also be demonstrated in rabbits by the Born test in vitro and ex vivo (method based on Nature, Vol. 194 (1962), pages 927–929) and by the fibre test according to Jacobi (method based on Thrombos. Diathes. haemorrh., Vol. 26 (1971), pages 192–202).

Compound I and its salts also increase the activity of the fibrinolytic system. This can be demonstrated by determining the euglobulin-lysis time in rabbits and can also be demonstrated in vitro by the "hanging clot" test according to von Kaulla, (J. Med. Chemistry, Vol. 8, (1965), pages 164–166).

Compound I and its physiologically acceptable salts have a long elimination half-life and, in contrast to substances which have a comparable action, prophylaxis against thrombosis can be achieved over the whole day with single daily dose.

Compound I and its salts can be administered for prophylaxis and therapy in patients where there is a risk of thrombosis in the venous region, e.g., Status varicosus and post-operative thromboembolic complications, and in patients where there is a risk of thrombosis in the arterial region, e.g., progressive arteriosclerotic processes, vascular surgery and reinfarct prophylaxis and infarct prophylaxis in cases of angina pectoris.

Examples of physiologically acceptable salts of Compound I are the sodium, potassium, magnesium, calcium and ammonium salts and also substituted ammonium salts, for example, the dimethylammonium, diethylammonium, monoethanolammonium, diethanolammonium, triethanolammonium, cyclohexylammonium, dicyclohexylammonium and dibenzylethylenediammonium salts.

For use in the method of the invention, compound I and its physiologically acceptable salts can be formulated into suitable pharmaceutically acceptable dosage forms, e.g., as a mixture with solid, liquid and/or semi-liquid excipients or auxiliaries. Excipients which can be used are organic or inorganic substances which are suitable for enteral or parenteral administration and do not react with the active compounds, for example, water, vegetable oils, benzyl alcohols, polyethylene glycols, gelatine, lactose, starch, magnesium stearate and talc. Formulations suitable for enteral administration are, for example, tablets, dragees, capsules, syrups, elixirs, drops or suppositories. Formulations used for parenteral administration are, in particular, solutions, preferably oily or aqueous solutions, and also suspensions, emulsions or implants. The active compounds can also be administered in a micro-encapsulated form. Furthermore, they can be lyophilized and the resulting lyophilizates can be used, for example, to prepare injectable formulations. The formulations mentioned can be sterilized and/or contain auxiliaries, such as lubricants, preservatives, stabilizers and/or wetting agents, emulsifiers, salts for regulating the osmotic pressure, buffer substances, dyestuffs, flavoring and/or aroma substances.

The pharmaceutical compositions comprising Compound I or a salt thereof can also contain one or more other physiologically active compound, preferably another compound having the same or a similar activity, for example, salicylic acid derivatives, e.g., ASA or its salts, other non-steroid antiphlogistic agents, e.g., Indomethacin, hypotensive agents, e.g., Diphyridamol, anticoagulants, e.g., Warfarin, antipodagric agents, e.g., sulphinepyrazone, $\beta$-blocking agents, e.g., propranolol, anti-histamines, e.g., Brompheniramin, prostaglandins, e.g., PGE 1, and vitamins, e.g., Vitamin C.

The novel pharmaceutical compositions of this invention comprise a thrombocyte aggregation inhibitory amount per unit dosage amount of a mixture of Compound I, or a physiologically acceptable salt thereof, and ASA, or a physiologically acceptable salt thereof, alone or in admixture with a solid, liquid or semi-liquid pharmaceutically acceptable carrier.

The molar ratio of ASA : I can be, for example, from about 60 : 1 to 0.1 : 1, preferably from 2 : 1 to 0.5 : 1, most preferably about 1 : 1. Such mixtures display a stronger effect on the thrombocyte adhesiveness in the fiber test according to Jacobi (for example, on intravenous administration to rabbits, dose 0.075 mg. of I and 0.0375 mg of ASA; method loc. cit.) than that expected from the additive effect of the individual components. A synergistic effect was also observed in the fiber test on rabbits when the two active compounds were administered together orally, as shown in Table 1.

TABLE 1

| Compound Administered | Dose mg/kg | No. of Animals | Thrombocyte Protein $\bar{X} \pm S_x (\mu g)$ | % Decrease* |
|---|---|---|---|---|
| Control | — | 6 | 30.92 ± 4.80 | — |
| ASA | 10 | 6 | 28.00 ± 9.40 | 9 |
| I | 20 | 6 | 21.79 ± 2.06 | 29 |
| ASA + I | 10 + 20 | 6 | 14.91 ± 1.95 | 52 |

*Compared with the control.

In the Born test (ex vivo; method, compare loc. cit.), the ADP-induced aggregation of thrombocytes was also inhibited in a synergistic manner on oral administration of both I and ASA, as shown in Table 2.

TABLE 2

| Substance | Dose mg/kg | No. of Animals | Change in Optical Density at 600 nm $\bar{X} \pm S_x$ | % Decrease* |
|---|---|---|---|---|
| Control | — | 6 | 0.222 ± 0.038 | — |
| ASA | 10 | 6 | 0.190 ± 0.029 | 14 |
| I | 20 | 6 | 0.147 ± 0.039 | 34 |
| ASA + I | 10 + 20 | 6 | 0.089 ± 0.035 | 60 |

*Compared with the control.

The acid I and its physiologically acceptable salts, which are administered in the method of this invention, are preferably administered in dosages of between about 1 and 500 mg., especially between 10 and 300 mg. per dosage unit. The daily dosage thereof is preferably between about 0.02 and 10, and especially between 0.2 and 6, mg/kg of body weight. The particular dose for each specific patient depends, however, on very diverse factors, for example on the effectiveness of the particular compound employed (the acid I or a specific salt), on the age, the body weight, the general state of health, the sex, the diet, on the time and route of administration, on the rate of elimination, the combination of medicaments and the severity of the particular disease to which the therapy applies. Oral administration is preferred.

A particularly preferred type of use for the prophylaxis of thromboses is the administration of a daily initial dose of about 200 to 300 mg (e.g., in five doses, each of 40 to 60 mg) and maintenance of the compound I level thus achieved by daily additional administrations of about 20 to 40 mg.

The compositions of the invention for oral administration preferably contain, per dosage unit, about 1 to 500, preferably 5 to 300, mg of ASA or salt thereof and about 1 to 300, preferably 5 to 40, mg of compound I or salt thereof.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE A - Tablets

A mixture of 1 kg of acid I, 4 kg of lactose, 1.2 kg of maize starch, 0.2 kg of talc and 0.1 kg of magnesium stearate is pressed to give tablets in the customary way, so that each tablet contains 20 mg of active compound.

Tablets with other active substance contents, e.g., of 10, 30, 50 or 100 mg, can be pressed from the same mixture.

EXAMPLE B - Dragées

Dragée cores are pressed in a similar manner to Example 1 and are then coated in the customary manner with a coating of cane sugar, potato starch, talc, tragacanth and a dyestuff and are administered in the same way as the tablets of Example 1.

EXAMPLE C - Capsules 5 kg. of the sodium salt of acid I are filled into hard gelatin capsules in the customary manner, so that each capsule contains 10 mg of the active compound.

EXAMPLE D - Ampoule for an injectable solution 1 kg of acid I is suspended in 10 liters of water and brought into solution using the calculated required amount of 0.1 N NaOH. The solution is sterile-filtered immediately and placed in injection ampoules, and then frozen and lyophilized in a freeze-drying unit. Each ampoule contains 10 mg. of I. In order to obtain an injectable solution, the contents of an ampoule are dissolved in 3 ml of water.

EXAMPLE 1 - Tablets (combination formulation)

100 g of ASA, 200 g of acid I, 20 kg of lactose, 5 kg of potato starch, 1 kg of talc and 0.5 kg of magnesium stearate are mixed and tablets, which each contain 10 mg of ASA and 20 mg of acid I, are pressed from the mixture in the customary manner.

EXAMPLE 2 - Tablets (combination formulation)

Tablets which each contain: a) 100 mg of ASA and 10 mg of I, b) 250 mg of ASA and 10 mg of I, c) 500 mg of ASA and 5 mg of I, d) 300 mg of ASA and 1 mg of I, e) 5 mg of ASA and 10 mg of I, f) 100 mg of ASA and 40 mg of I and g) 100 mg of ASA and 300 mg of I are prepared in the same manner as in Example 1.

EXAMPLE 3 - Dragées (combination formulation)

A mixture of 1.5 kg of I, 20 kg of ASA, 0.45 kg of finely dispersed silica, 3.7 kg of cellulose powder, 0.65 kg of calcium stearate and 18.7 kg of lactose is pressed to give dragée cores, which are then coated in the customary manner with a coating of cane sugar, potato starch, talc, tragacanth and a dyestuff and are administered in the same way as the tablets of Example 1 or 2. Each dragée contains 200 mg of ASA and 15 mg of I.

EXAMPLE 4 - Dragées (combination formulation)

100 kg of I, 200 kg of ASA, 8 kg of finely divided silica, 60 kg of methylcellulose, 9 kg of talc and 323 kg of lactose are mixed, the mixture is pressed to give dragée cores and the cores are coated with a dragée coating in the customary manner. Each dragee contains 100 mg of I and 200 mg of ASA.

EXAMPLE 5 - Capsules (combination formulation)

4.16 kg of the sodium salt of acid I and 1.80 kg of ASA are mixed and the mixture is filled into hard gelatin capsules in the customary manner, so that each capsule contains 20.8 mg and 9 mg, respectively, of the two active compounds.

EXAMPLE 6 - Tablets, dragées and capsules (combination formulation)

Tablets, dragées or capsules are prepared in the same way as in Example 1, 2, 3, 4 or 5 but the ASA is in a microencapsulated form.

EXAMPLE 7 - Ampoule for an injectable solution (combination formulation)

1 kg of I is suspended in 10 liters of water and brought into solution using the calculated amount of 0.1 N NaOH. A solution of 3.62 kg of the lysine salt of ASA in 10 liters of water is added to this solution and the mixture is sterile-filtered, placed in ampoules, frozen and lyophilized. Each ampoule contains 10 mg of I and 20 mg of ASA (in the form of the lysine salt).

EXAMPLE 8 - Clinical use of acid I

A male patient of 70 kg body weight suffering from an acute superficial thrombophlebitis in the lower leg with all typical symptoms of this disease (calor, rubor, dolor) is treated orally with an initial dose of 300 mg of compound I. During the following 10 days, he receives 30 mg daily of compound I orally.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising a mixture of (a) a thrombocyte aggregation inhibiting amount per unit dosage of 2-(4,5-bis-p-chlorophenyl-oxazol-2-yl-mercapto)-propionic acid, or a physiologically acceptable salt thereof, and (b) acetylsalicylic acid or a physiologically acceptable salt thereof, in a molar ratio of (b) to (a) of from 60:1 to 0.1:1.

2. A composition according to claim 1 wherein the molar ratio therein of (b) to (a) is from 2:1 to 0.5:1.

3. A composition according to claim 1 wherein the molar ratio therein of (b) to (a) is about 1:1.

4. A composition according to claim 1 adapted for oral administration containing per dosage unit 5 to 300 mg of (b) and 5 to 40 (a).

5. A composition according to claim 4 in the form of tablets, dragées or capsules.

6. A composition according to claim 5 wherein both (a) and (b) are present therein as free acids.

7. A method of inhibiting thrombocyte aggregation in human patients in which there exists a high risk of arterial or venous thrombosis, which comprises administering thereto an amount of 2-(4,5-bis-p-chlorophenyl-oxazol-2-yl-mercapto)-propionic acid or a physiologically acceptable salt thereof, effective to inhibit thrombocyte aggregation.

8. A method according to claim 7 wherein the propionic acid or salt thereof is administered orally.

9. A method according to claim 7 wherein the propionic acid or salt thereof is administered daily.

10. A method according to claim 7 wherein the propionic acid or salt thereof is administered in admixture with acetylsalicylic acid or a physiologically acceptable salt thereof in a molar ratio of the latter to the former of from 2:1 to 0.5:1.

11. A method according to claim 10 wherein the molar ratio is about 1:1.

12. A method according to claim 10 wherein the mixture is administered orally.

13. A method according to claim 10 wherein the mixture is administered daily.

* * * * *